(12) United States Patent
Cannon et al.

(10) Patent No.: US 11,273,082 B2
(45) Date of Patent: Mar. 15, 2022

(54) TECHNIQUES FOR URINE AND FECES CONTAINMENT BRIEF WITH SLING

(71) Applicants: Kathleen Cannon, Bluffdale, UT (US); Nisha Cannon Harman, Midvale, UT (US); Marianne Rupper Kendrick, Bluffdale, UT (US)

(72) Inventors: Kathleen Cannon, Bluffdale, UT (US); Nisha Cannon Harman, Midvale, UT (US); Marianne Rupper Kendrick, Bluffdale, UT (US)

( * ) Notice: Subject to any disclaimer, the term of this patent is extended or adjusted under 35 U.S.C. 154(b) by 205 days.

(21) Appl. No.: 16/166,056

(22) Filed: Oct. 19, 2018

(65) Prior Publication Data

US 2019/0151165 A1 May 23, 2019

Related U.S. Application Data

(60) Provisional application No. 62/574,589, filed on Oct. 19, 2017.

(51) Int. Cl.
*A61F 13/475* (2006.01)
*A61F 13/49* (2006.01)
(Continued)

(52) U.S. Cl.
CPC ...... *A61F 13/475* (2013.01); *A61F 13/49004* (2013.01); *A61F 13/494* (2013.01);
(Continued)

(58) Field of Classification Search
CPC .................. A61F 13/495; A61F 13/511; A61F 13/49009; A61F 13/49473; A61F 13/515;
(Continued)

(56) References Cited

U.S. PATENT DOCUMENTS 4,687,679 A * 8/1987 Beale .................. C08J 7/123
427/488
4,968,312 A * 11/1990 Khan .................. A61F 13/4915
604/385.13
(Continued)

*Primary Examiner* — Michele M Kidwell
(74) *Attorney, Agent, or Firm* — Jefferson IP Law, LLP; Raymond B. Persino

(57) ABSTRACT

Provided is a containment brief to be worn by a user for containing urine and feces. The containment brief includes a strip of stretchable resilient material having a first end and a second end, a first stretchable resilient side panel attached to the strip of stretchable resilient material along a first side of the strip of stretchable resilient material between the first end and the second end, a second stretchable resilient side panel attached to the strip of stretchable resilient material along a second side of the strip of stretchable resilient material between the first end and the second end, the first side of the strip of stretchable resilient material being opposite the second side of the strip of stretchable resilient material, a first side dam disposed along the first side of the strip of stretchable resilient material, a second side dam disposed along the second side of the strip of stretchable resilient material, an absorbent pad disposed on a first surface of the strip of stretchable resilient material, the absorbent pad including a rectangular cut-out therein, and a sling disposed on the absorbent pad at least partially around the rectangular cut-out, wherein each of the first stretchable resilient side panel and the second stretchable resilient side panel includes at least one adhesive tab.

11 Claims, 3 Drawing Sheets

(51) Int. Cl.
  *A61F 13/494* (2006.01)
  *A61F 13/495* (2006.01)
  *A61F 13/15* (2006.01)
  *A61F 13/513* (2006.01)
(52) U.S. Cl.
  CPC ...... *A61F 13/495* (2013.01); *A61F 13/49007* (2013.01); *A61F 13/49446* (2013.01); *A61F 13/513* (2013.01); *A61F 2013/15121* (2013.01); *A61F 2013/49025* (2013.01); *A61F 2013/4951* (2013.01); *A61F 2013/49076* (2013.01)
(58) Field of Classification Search
  CPC ............ A61F 13/5633; A61F 13/49413; A61F 2013/49092; A61F 2013/49493; A61F 2013/4951; A61F 2013/4953; A61F 2013/4956; A61F 13/475; A61F 13/49446; A61F 13/49004; A61F 13/49007; A61F 13/513; A61F 13/494; A61F 2013/49076; A61F 2013/15121; A61F 2013/49025; A61F 2013/51195
  See application file for complete search history.

(56) References Cited

U.S. PATENT DOCUMENTS

| | | | | |
|---|---|---|---|---|
| 5,062,840 A | * | 11/1991 | Holt | A61F 13/495 604/385.19 |
| 5,397,316 A | * | 3/1995 | LaVon | A61F 13/535 604/369 |
| 5,873,868 A | * | 2/1999 | Nakahata | A61F 13/49011 604/358 |
| 7,122,024 B2 | * | 10/2006 | Nakajima | A61F 13/49019 604/385.25 |
| 9,445,951 B2 | * | 9/2016 | Moberg-Alehammar | A61F 13/511 |
| 10,441,481 B2 | * | 10/2019 | Bianchi | A61F 13/534 |
| 2002/0026168 A1 | * | 2/2002 | Yagou | A61F 13/512 604/378 |
| 2007/0255245 A1 | * | 11/2007 | Asp | A61F 13/532 604/385.19 |
| 2008/0065038 A1 | * | 3/2008 | Sugiyama | A61F 13/515 604/385.04 |

* cited by examiner

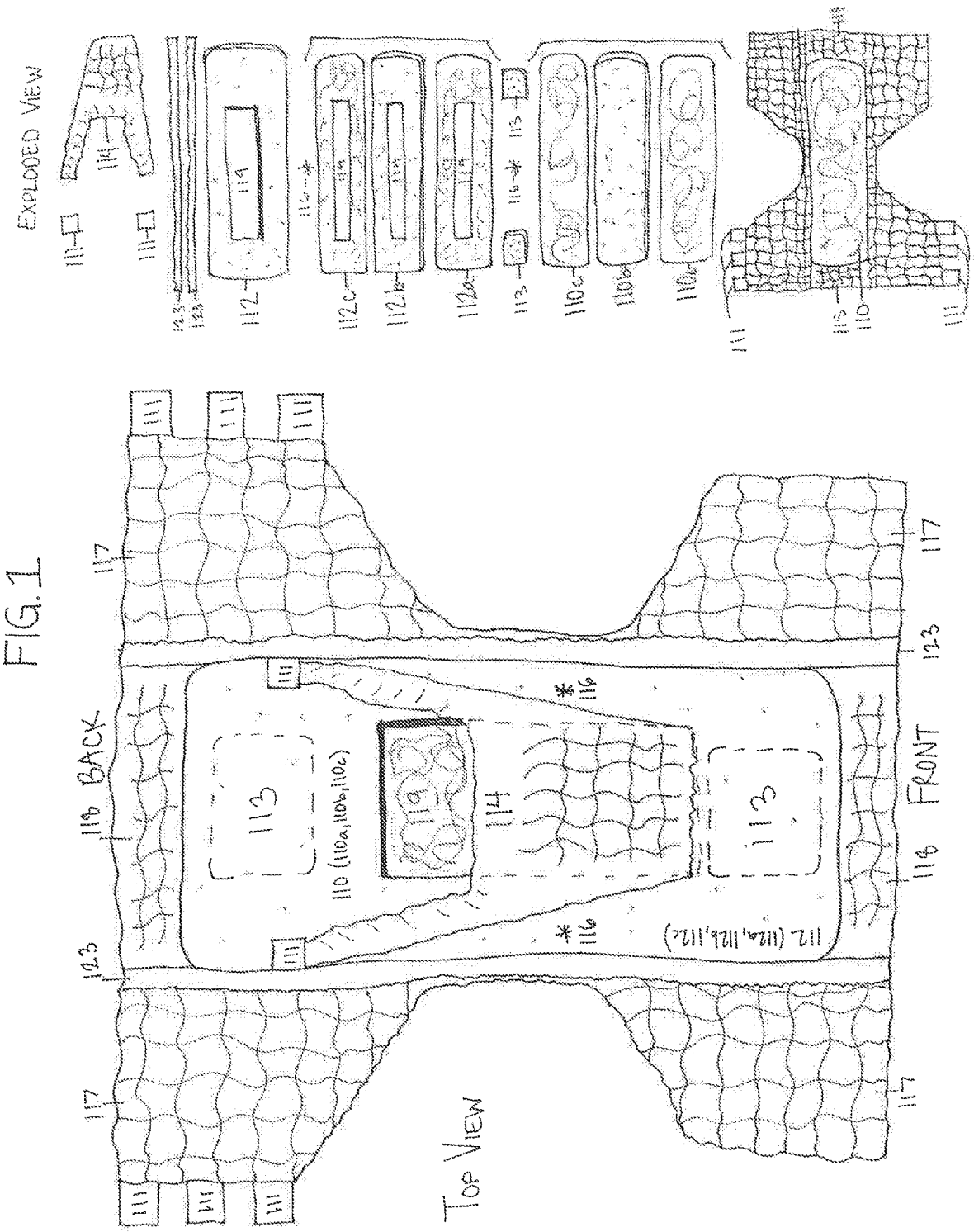

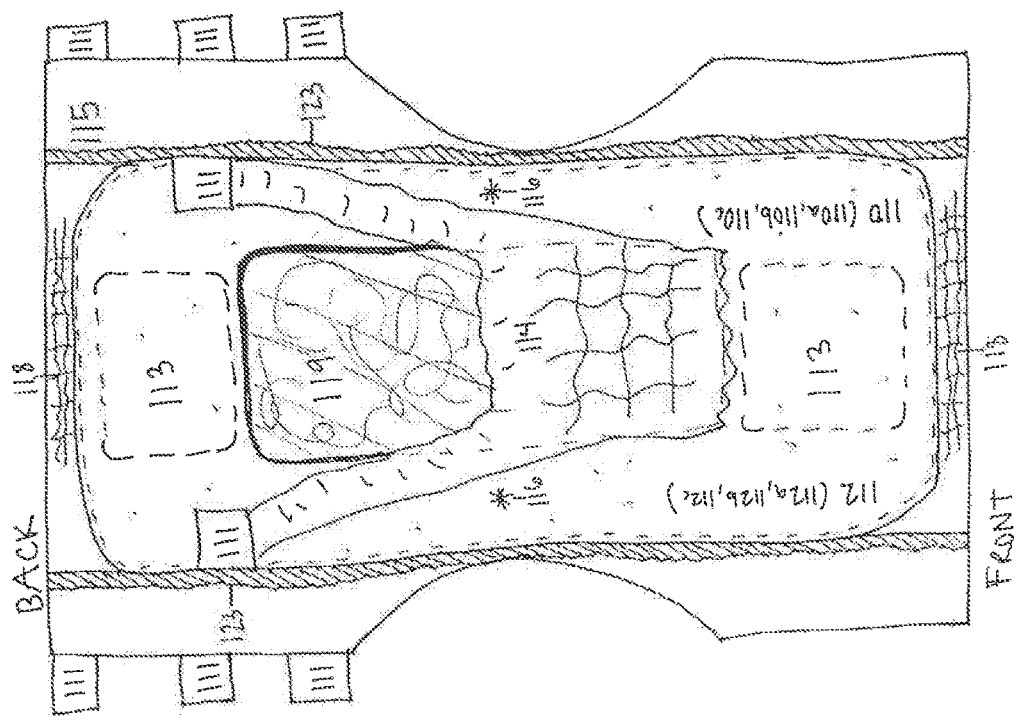

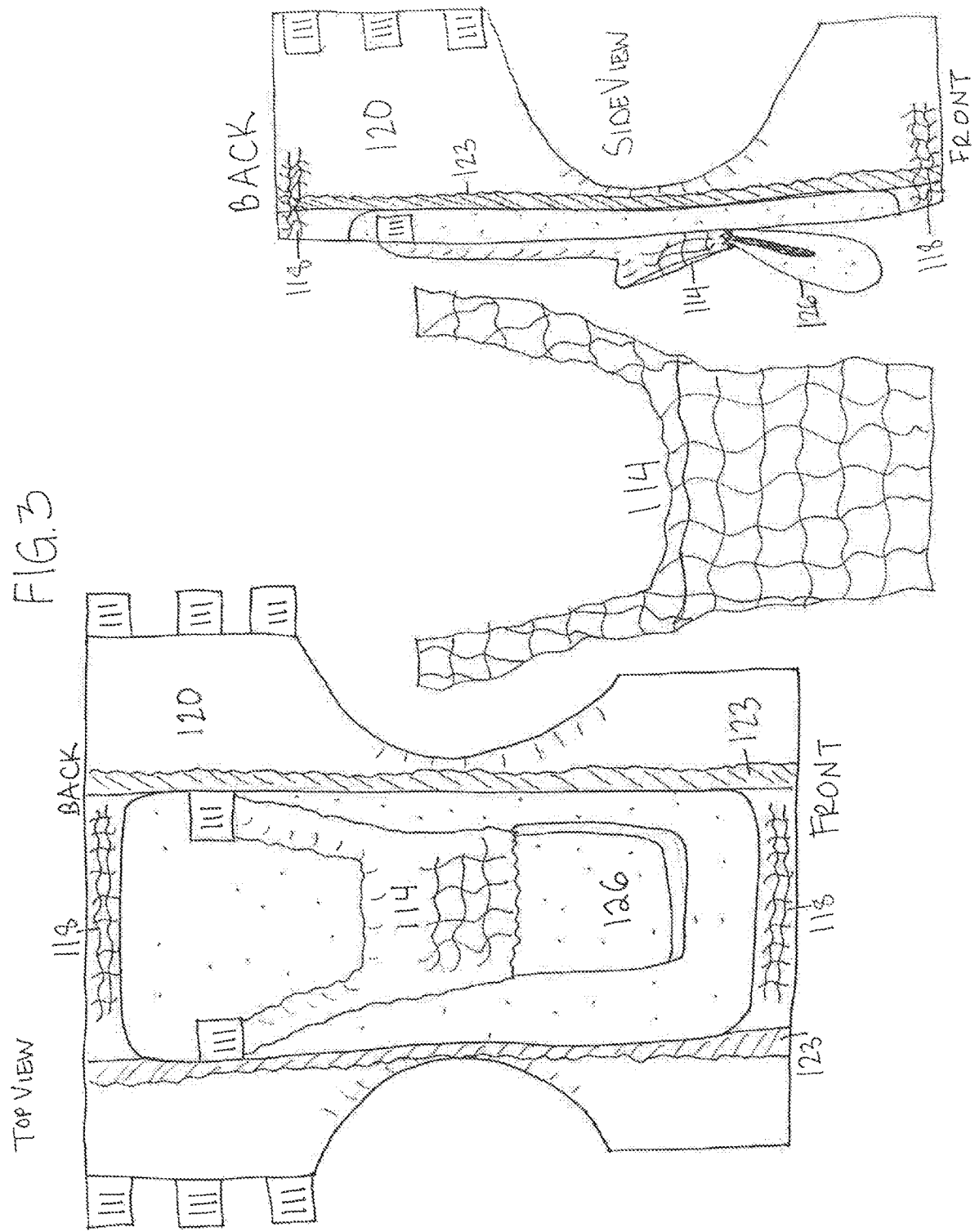

TECHNIQUES FOR URINE AND FECES CONTAINMENT BRIEF WITH SLING

CROSS-REFERENCE TO RELATED APPLICATION

This application is based on and claims priority under 35 U.S.C. § 119(e) of a U.S. Provisional application Ser. No. 62/574,589, filed on Oct. 19, 2017, in the U.S. Patent and Trademark Office, the disclosure of which is incorporated by reference herein in its entirety.

BACKGROUND

1. Field

The present disclosure relates to techniques for a urine and feces containment brief with a sling.

2. Description of the Related Art

Often individuals with special medical needs who must wear urine and feces containment briefs soil themselves, their clothing, bedding, wheelchairs and any other item they might come in contact with. This is unsanitary and poses a health risk to both the individual and their caregivers. This soiling can go completely up the individuals back or stomach and sometimes as far as their neck or down to their knees. Urine and feces containment briefs of the related art have attempted to address this soiling, but their effectiveness has fallen short.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide a urine and feces containment brief which will protect a user from urine and feces leakage onto their clothing, bedding and other surfaces.

Another aspect of the present disclosure is to provide a urine and feces containment brief that increases the quality of life for a user and reduces the amount of work for a caregiver.

Another aspect of the present disclosure is to provide a urine and feces containment brief that maintains the health of both a user and a caregiver by less exposure to human waste.

Additional aspects will be set forth in part in the description which follows and, in part, will be apparent from the description, or may be learned by practice of the presented embodiments.

In accordance with an aspect of the disclosure, a containment brief to be worn by a user for containing urine and feces is provided. The containment brief includes a strip of stretchable resilient material having a first end and a second end, a first stretchable resilient side panel attached to the strip of stretchable resilient material along a first side of the strip of stretchable resilient material between the first end and the second end, a second stretchable resilient side panel attached to the strip of stretchable resilient material along a second side of the strip of stretchable resilient material between the first end and the second end, the first side of the strip of stretchable resilient material being opposite the second side of the strip of stretchable resilient material, a first side dam disposed along the first side of the strip of stretchable resilient material, a second side dam disposed along the second side of the strip of stretchable resilient material, an absorbent pad disposed on a first surface of the strip of stretchable resilient material, the absorbent pad including a rectangular cut-out therein, and a sling disposed on the absorbent pad at least partially around the rectangular cut-out, wherein each of the first stretchable resilient side panel and the second stretchable resilient side panel includes at least one adhesive tab.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 1 illustrates a urine and feces containment brief according to a first embodiment of the disclosure;

FIG. 2 illustrates a urine and feces containment brief according to a second embodiment of the disclosure; and FIG. 3 illustrates a urine and feces containment brief according to a third embodiment of the disclosure.

The same reference numerals are used to represent the same elements throughout the drawings.

DETAILED DESCRIPTION

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

FIGS. 1 through 3, discussed below, and the various embodiments used to describe the principles of the present disclosure in this patent document are by way of illustration only and should not be construed in any way that would limit the scope of the disclosure. Those skilled in the art will understand that the principles of the present disclosure may be implemented in any suitable arrangement. The terms used to describe various embodiments are exemplary. It should be understood that these are provided to merely aid the understanding of the description, and that their use and definitions in no way limit the scope of the present disclosure. Terms first, second, and the like are used to differentiate between objects having the same terminology and are in no way intended to represent a chronological order, unless where explicitly stated otherwise. A set is defined as a non-empty set including at least one element.

FIG. 1 illustrates a urine and feces containment brief according to a first embodiment of the disclosure.

With reference to FIG. 1, the urine and feces containment brief 120 may include an absorbent article 110 that may include a backsheet 110a, a super absorbent polymer core 110b and a topsheet 110c which may be made from industry materials of the related art or bamboo. The shape of absorbent article 110 may be rectangular, T-shaped or I-shaped.

A layer of congruent padding 112 that may be comprised of a permeable backsheet 112a, a super absorbent polymer core 112b, and a topsheet 112c may be layered on top of the absorbent article 110 and may be made from industry materials of the related art or bamboo. The layer of congruent padding 112 may be attached on the outer perimeter of absorbent article 110 by at least one of stitching, heat-sealing, or another attachment technique, but the disclosure is not limited thereto.

The layer of congruent padding 112 may have a rectangular cut-out 119 approximately, but not limited to, 55% of the length and 33% of the width of the layer of congruent padding 112 positioned off-center, closer to the back portion of the layer of congruent padding 112 helping to ensure the anus of the wearer is within the rectangular cut-out 119, which may allow feces and urine to flow in between absorbent article 110 and layer of congruent padding 112, trapping and absorbing the urine and feces.

A stitch 116 may be placed half way down on both long sides of the layer of congruent padding 112 to allow the rectangular cut-out 119 to lay relatively flat, increasing comfort and avoiding excessive bunching.

An absorbent pad 113 measuring approximately, but not limited to, 5 inches by 5 inches, may be attached on both the front and back portions of absorbent article 110, underneath the congruent padding 112 as an extra measure to help absorb large amounts of feces and urine.

A substantially stretchable resilient side panel 117 allows for a customized and comfortable fit, allowing the article to be worn by a wider range of individuals weighing between 120-250+lbs. The side panel 117 may be present on all 4 sides, or just 2 sides. The side panel 117 may be attached by at least one of stitching, heat-sealing, or another attachment technique, but the disclosure is not limited thereto. The side panel 117 may be made from materials of the related art, bamboo or other suitable material.

A side dam 123 made from bamboo or another suitable nonwoven material, may have a gather along the top edge and extends along both edges of the congruent padding 112 from the back to the front. The side dam helps keep waste from leaking out of the absorbent area and onto the wearers clothing before it has time to be absorbed.

A strip of stretchable resilient material 118 such as elastic, may be attached to both the top edge and bottom edge of absorbent article 110 as another measure to help keep the feces contained. The stretchable resilient material 118 may be attached by at least one of stitching, heat-sealing, or another attachment technique, but the disclosure is not limited thereto.

Three adhesive tabs 111 may be attached to the outside edge of the stretchable resilient side panels 117 that may be attached to the back portion of the absorbent article 110 by at least one of stitching, heat-sealing, or another attachment technique, but the disclosure is not limited thereto. The purpose of the third tab may be to help secure the urine and feces containment brief 120 around the hip and the leg joint, helping to prevent leakage and to create a customized and comfortable fit.

The urine and feces containment brief 120 for males may also have a sling 114 made of stretchy resilient material, that may be attached to the layer of congruent padding 112 by at least one of stitching, heat-sealing, or another attachment technique, but the disclosure is not limited thereto, in front of the rectangular cut-out 119. The sling 114 may have two straps that stretch up and over the pelvis of the wearer and may attach to the layer of congruent padding 112 with an adhesive tab 111 for each strap. The sling 114 creates a pouch for the penis to be held in, helping to prevent it from jutting out the side of the urine and feces containment brief 120 and leaking urine onto other surfaces.

When the urine and feces containment brief 120 is in place on the individual, it should fit snugly and comfortably enough to stay in place and prevent urine and feces leakage from coming out of the urine and feces containment brief 120. It may have significant room and absorbency to contain the contents of the individuals' bowel movements and urine, decreasing the chance of waste leaking out onto the wearer and their surroundings. Removing the urine and feces containment brief 120 when the waste is contained may be is much easier and sanitary, helping to maintain the health and dignity of both the wearer and caregiver.

FIG. 2 illustrates a urine and feces containment brief according to a second embodiment of the disclosure.

With reference to FIG. 2, the urine and feces containment brief 120 may include an absorbent article 110 that may include a backsheet 110a, a super absorbent polymer core 110b, and a topsheet 110c which may be made from materials of the related art or bamboo. The shape of absorbent article 110 may be rectangular, T-shaped or I-shaped.

A layer of congruent padding 112 comprised of a permeable backsheet 112a, a super absorbent polymer core 112b, and a topsheet 112c may be layered on top of the absorbent article 110 and may be made from materials of the related art or bamboo. The layer of congruent padding 112 may be attached on the outer perimeter of absorbent article 110 by at least one of stitching, heat-sealing, or another attachment technique, but the disclosure is not limited thereto.

The layer of congruent padding 112 may have a rectangular cut-out 119 approximately, but not limited to, 55% of the length and 33% of the width of the layer of congruent padding 112 positioned off-center, closer to the back portion of the layer of congruent padding 112 helping to ensure the anus of the wearer is within the rectangular cut-out 119. This configuration may allow feces and urine to flow in between absorbent article 110 and layer of congruent padding 112, trapping and absorbing the urine and feces.

A stitch 116 may be placed half way down on both long sides of the layer of congruent padding 112 to allow the rectangular cut-out 119 to lay relatively flat, thereby increasing comfort and avoiding excessive bunching.

An absorbent pad 113 measuring approximately, but not limited to, 5 inches by 5 inches, may be attached on both the front and back portions of absorbent article 110, underneath the layer of congruent padding 112 as an extra measure to help absorb large amounts of feces and urine.

A breathable backsheet 115 made from materials of the related art or bamboo, may be attached to the underside of absorbent article 110 and may be attached by at least one of stitching, heat-sealing, or another attachment technique, but the disclosure is not limited thereto.

A side dam 123 made from bamboo or other suitable nonwoven material, may have a gather along the top edge and extends along both edges of the congruent padding 112 from the back to the front. The side dam helps keep waste from leaking out of the absorbent area and onto the wearers clothing before it has time to be absorbed.

A strip of stretchable resilient material 118 such as elastic, may be attached to both the top edge and bottom edge of absorbent article 110 as another measure to help keep the feces contained. The stretchable resilient material 118 may be attached by at least one of stitching, heat-sealing, or another attachment technique, but the disclosure is not limited thereto.

Three adhesive tabs 111 may be attached to the outside edge of the breathable backsheet 115 by at least one of stitching, heat-sealing, or another attachment technique, but the disclosure is not limited thereto. The purpose of the third tab may be to help secure the urine and feces containment brief 120 around the hip and the leg joint, helping to prevent leakage and to create a customized and comfortable fit.

The urine and feces containment brief 120 for males may also have a sling 114 made of stretchy resilient material, attached to the layer of congruent padding 112 by at least one of stitching, heat-sealing, or another attachment technique, but the disclosure is not limited thereto, in front of the rectangular cut-out 119. The sling 114 may have two straps that stretch up and over the pelvis of the wearer and may attach to the layer of congruent padding 112 with an adhesive tab 111 for each. The sling 114 creates a pouch for the penis to be held in, helping to prevent it from jutting out the side of the urine and feces containment brief 120 and leaking urine onto other surfaces.

FIG. 3 illustrates a urine and feces containment brief according to a third embodiment of the disclosure.

With reference to FIG. 3, a urine and feces containment brief 120 may include three adhesive tabs 111 on each side of the back portion of the urine and feces containment brief 120. The purpose of the third tab may be to help secure the urine and feces containment brief 120 around where the hip and the leg join to prevent leakage.

A sling 114 made of stretchy resilient material comprised of bamboo or other suitable material may be attached to the center bottom of the urine and feces containment brief 120. Two straps extending from the sling 114 may stretch up and over the pelvis of the wearer and attach to the inside back of the urine and feces containment brief 120 with an adhesive tab 111 for each strap, creating a pouch for the penis to be held in, helping to prevent it from jutting out the side of the urine and feces containment brief 120 and leaking urine onto the wearer and other surfaces.

A rectangular absorbent pad 126 approximately, but not limited to, 3 inches by 10 inches may be folded in half with the two aligned ends attached to the front portion of the urine and feces containment brief 120 approximately ⅓ length from the front portion of the urine and feces containment brief 120, by at least one of stitching, heat-sealing, or another attachment technique, but the disclosure is not limited thereto. The sling 114 may be attached at the base of the absorbent pad 126 on the posterior side, either by at least one of stitching, heat-sealing, or another attachment technique, but the disclosure is not limited thereto. When the urine and feces containment brief 120 is positioned properly on the wearer with the sling 114 may stretched up over the pelvis and may attached to the adhesive tabs 111, the absorbent pad 126 may rest against the sling and the penis so that when urine is excreted it may contact the absorbent pad 126 and then the urine and feces containment brief 120, preventing the urine from exiting the urine and feces containment brief 120 through the front, back and leg area, keeping the clothing and other items in contact with the wearer dry.

A strip of stretchable resilient material 118 such as elastic, may be attached to both the top edge and bottom edge of diaper 120 as another measure to help keep the urine and feces contained. The stretchable resilient material 118 may be attached by at least one of stitching, heat-sealing, or another attachment technique, but the disclosure is not limited thereto.

Substantially stretchable resilient side panels 117 may be included to increase the comfort and accommodate a larger size range of wearers.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A containment brief to be worn by a user for containing urine and feces, the containment brief comprising:
   a strip having a first end and a second end;
   a first side panel attached to the strip along a first side of the strip between the first end and the second end;
   a second side panel attached to the strip along a second side of the strip between the first end and the second end, the first side of the strip being opposite the second side of the strip;
   a first side dam disposed along the first side of the strip;
   a second side dam disposed along the second side of the strip;
   an absorbent article disposed on a first surface of the strip, the absorbent article including a backsheet, an absorbent core, and a topsheet;
   a layer of congruent padding including a backsheet, an absorbent core, and a topsheet, the layer of congruent padding being attached to the absorbent article at a perimeter of the absorbent article, the layer of congruent padding including a cut-out therein; and
   a sling in which a first end thereof is disposed on the layer of congruent padding at least partially around the cut-out, the sling including two straps extending from a second end thereof that each include a first adhesive tab,
   wherein the cut-out allows for the urine and the feces to be deposited and dispersed between the absorbent article and the layer of congruent padding to thereby mitigate the urine and the feces from moving beyond bounds of the containment brief,
   wherein each of the first side panel and the second side panel includes at least one second adhesive tab, and wherein first adhesive tab of each of the two straps of the sling is configured to attach to the layer of congruent padding at an inside back of the containment brief so the two straps stretch up and over a pelvis of the user for the sling to create a pouch to hold a penis of user in a position to thereby mitigate the urine from moving beyond bounds of the containment brief.

2. The containment brief of claim 1, further comprising:
at least one absorbent pad disposed on the absorbent article between the absorbent article the layer of congruent padding at at least one of a front end portion or a rear end portion.

3. The containment brief of claim 2, wherein the at least one absorbent pad is one of square or rectangular.

4. The containment brief of claim 1, further comprising:
an attachment, through the layer of congruent padding to the absorbent article, disposed between longitudinal sides of the cut-out and a perimeter of the layer of congruent padding.

5. The containment brief of claim 1, wherein the cut-out is rectangular.

6. The containment brief of claim 1, wherein the strip comprises a stretchable resilient material.

7. The containment brief of claim 1,
wherein the first side panel comprises a stretchable resilient material, and
wherein the second side panel comprises a stretchable resilient material.

8. A containment brief to be worn by a user for containing urine and feces, the containment brief comprising:
a strip having a first end and a second end;
a first side panel attached to the strip along a first side of the strip between the first end and the second end;
a second side panel attached to the strip along a second side of the strip between the first end and the second end, the first side of the strip being opposite the second side of the strip;
a first side dam disposed along the first side of the strip;
a second side dam disposed along the second side of the strip material;
an absorbent article disposed on a first surface of the strip, the absorbent article including a backsheet, an absorbent core, and a topsheet;
a sling in which a first end thereof is disposed on the absorbent article, the sling including two straps extending from a second end thereof that each include a first adhesive tab; and
a absorbent pad disposed on the absorbent article,
wherein each of the first side panel and the second side panel includes at least one second adhesive tab, and
wherein the first adhesive tab of each of the two straps of the sling is configured to attach to the absorbent article at an inside back of the containment brief so the two straps stretch up and over a pelvis of the user for the sling to create a pouch to hold a penis of user in a position such that the urine will be directed to the absorbent pad to thereby mitigate the urine from moving beyond bounds of the containment brief.

9. The containment brief of claim 8, wherein the absorbent pad is one of square or rectangular.

10. The containment brief of claim 8, wherein the strip comprises a stretchable resilient material.

11. The containment brief of claim 8,
wherein the first side panel comprises a stretchable resilient material, and
wherein the second side panel comprises a stretchable resilient material.

* * * * *